(12) United States Patent
Evans et al.

(10) Patent No.: US 9,468,724 B2
(45) Date of Patent: Oct. 18, 2016

(54) NEEDLE SHIELD REMOVAL TOOL

(71) Applicant: West Pharmaceutical Services, Inc., Exton, PA (US)

(72) Inventors: Christopher Evans, Long Valley, NJ (US); Christopher Gieda, Long Valley, NJ (US); Brian Costello, Whitehouse Station, NJ (US)

(73) Assignee: WEST PHARMACEUTICAL SERVICES, INC., Exton, PA (US)

(*) Notice: Subject to any disclaimer, the term of this patent is extended or adjusted under 35 U.S.C. 154(b) by 0 days.

(21) Appl. No.: 14/422,883

(22) PCT Filed: Aug. 19, 2013

(86) PCT No.: PCT/US2013/055535
§ 371 (c)(1),
(2) Date: Feb. 20, 2015

(87) PCT Pub. No.: WO2014/031521
PCT Pub. Date: Feb. 27, 2014

(65) Prior Publication Data
US 2015/0238704 A1    Aug. 27, 2015

Related U.S. Application Data

(60) Provisional application No. 61/684,969, filed on Aug. 20, 2012.

(51) Int. Cl.
*A61M 5/32* (2006.01)
(52) U.S. Cl.
CPC .......... *A61M 5/3204* (2013.01); *A61M 5/3202* (2013.01); *A61M 5/3213* (2013.01); *A61M 2005/3215* (2013.01); *Y10T 29/53796* (2015.01)

(58) Field of Classification Search
CPC .......... A61M 5/3204; A61M 5/3202; A61M 5/3213; A61M 2005/3215; Y10T 29/53796
See application file for complete search history.

(56) References Cited

U.S. PATENT DOCUMENTS

| 4,915,225 A | 4/1990 | Tabor, Jr. et al. |
| 5,087,249 A | 2/1992 | Deal |

(Continued)

FOREIGN PATENT DOCUMENTS

| GB | 2465390 A | 5/2010 |
| GB | 2469671 A | 10/2010 |

(Continued)

OTHER PUBLICATIONS

Int'l Search Report dated Oct. 15, 2013 in Int'l Application No. PCT/US2013/055535.

(Continued)

*Primary Examiner* — Emily Schmidt
*Assistant Examiner* — Lauren M Peng
(74) *Attorney, Agent, or Firm* — Panitch Schwarze Belisario & Nadel LLP

(57) ABSTRACT

A removal tool for a needle shield includes an attachment cavity having an interior wall extending along a length of the attachment cavity and accessible via a sidewall aperture. The interior wall is sized to receive and engage the needle shield. A pull ring is connected to and extends from a proximal end of the attachment cavity. The pull ring has an exterior wall extending along an outer circumference of the pull ring and an interior wall extending along an inner circumference of the pull ring. The inner circumference is sized to accommodate at least one finger of a user.

16 Claims, 3 Drawing Sheets

(56) References Cited

U.S. PATENT DOCUMENTS

| | | |
|---|---|---|
| 5,143,414 A | 9/1992 | Rosellini |
| 5,183,469 A | 2/1993 | Capaccio |
| 5,512,049 A | 4/1996 | Fallas |
| 8,460,268 B2* | 6/2013 | Hedgepeth ............ A61J 1/1412 215/386 |
| 2009/0182284 A1* | 7/2009 | Morgan .............. A61M 5/3137 604/198 |

FOREIGN PATENT DOCUMENTS

| | | |
|---|---|---|
| WO | 03051423 A2 | 6/2003 |
| WO | 2012164397 A1 | 12/2012 |

OTHER PUBLICATIONS

Int'l Preliminary Report on Patentability issued Mar. 5, 2015 in Int'l Application No. PCT/US2013/055535.

* cited by examiner

NEEDLE SHIELD REMOVAL TOOL

CROSS-REFERENCE TO RELATED APPLICATION

This application is a Section 371 of International Application No. PCT/US2013/055535, filed Aug. 19, 2013, which was published in the English language on Feb. 27, 2014, under International Publication No. WO 2014/031521 A1, and the disclosure of which is hereby incorporated by reference in its entirety.

BACKGROUND OF THE INVENTION

The present invention relates generally to syringes and, more particularly, to a tool for removing syringe needle shields.

Syringes are known in the art as medical devices utilizable for delivering medicament to a patient. Syringes typically include a barrel component and a plunger component. During injection, the plunger forces the medicament out of a distal end of the barrel, through an elongated needle having an interior bore, out of a tip located at the distal end of the needle and into a patient. The needle tip has a geometry that allows the needle to easily puncture a patient's skin and penetrate tissue or a vein. In order to prevent a needle stick, or damage or contamination of the needle tip, syringe assemblies typically include a syringe needle shield, which is essentially a cover that is placed over the needle to enclose the needle tip. The shield also prevents a needle stick before and after using the syringe.

However, the act of removing a needle shield from a syringe assembly is a significant contributor to accidental needle stick injuries. Using both hands, a user typically pulls apart the needle shield from the syringe assembly. When the needle shield is released from the syringe assembly, the user's body reflexes to compensate for the sudden movement caused by the removal. Both of the user's hands often recoil, directing the exposed needle tip back toward the user's hand that is holding the removed needle shield, sometimes causing the exposed needle tip to inadvertently stick the user. In addition to being painful, the inadvertent needle stick can transmit diseases, such as HIV or Hepatitis, if the needle is contaminated. Previous developments have attempted to address this problem.

U.S. Pat. No. 4,915,225 to Tabor, Jr. et al, describes a counter-top mounted needle shield removal device which has two elongated U-shaped cavities, each of which may receive a needle shield that is capped onto a distal end of a syringe barrel. After the needle shield is inserted into a cavity of the removal device at an acute angle, a compression spring within the removal device pushes a distal end of the needle shield toward a proximal end of the cavity. As the needle shield is pushed by the spring, a proximal end of the needle shield engages a mechanical stop located at the proximal end of the cavity. The spring pressure and the mechanical stop effectively lock the needle shield within the cavity so a user can then pull the syringe barrel away from the needle shield with one hand.

If a needle shield is too long, the cavity can not receive and hold the needle shield. If a needle shield is too short, there is insufficient spring pressure to properly secure the needle shield within the cavity. Requiring a compression spring increases manufacturing difficulty and cost. The device must also be mounted to a wall or counter top, which limits the convenience and operability to a user.

U.S. Pat. No. 5,183,469 to Capaccio discloses a mounted needle shield removal tool having a single cylindrical cavity that receives a needle shield. A needle shield is inserted into a proximal end of the cavity and is twisted to engage internal screw threads at a distal end of the cavity, creating a mechanical lock that anchors the needle shield within the removal device. Once the needle shield is anchored, the user can pull the syringe barrel away from the removal device. If the screw threads within the removal tool cannot engage or do not fully engage the needle shield, the device is rendered inoperable. Hand operation alone is unsuitable because the device must be mounted to a surface, limiting convenience to the user.

U.S. Pat. No. 5,512,049 to Fallas discloses a mounted needle shield removal tool comprising two parallel plates, each having U-shaped arms that extend outwardly in the same direction. A space is provided between the parallel plates for receiving a flange on a needle shield. The top U-shaped plate has an extension, which is secured to a table top. After inserting the flange of the needle shield into the space between the parallel plates, the user pulls on the syringe barrel with one hand. The proximal end of the flange engages a distal end of the top U-shaped plate, preventing the needle shield from moving with the syringe barrel, which separates the syringe barrel from the needle shield. This device can only be used with needle shields that include a suitably sized flange. Hand operation alone is unsuitable because the device must be mounted to a surface, limiting convenience to the user.

U.S. Pat. No. 5,087,249 to Deal discloses a hand operated needle shield removal and attachment device comprising clips that define a C-shaped cavity. The clips surround a portion of a outer wall of a needle shield. A handle on the attachment device extends from the C-shaped cavity toward a proximal end of a syringe barrel. The handle allows the user to attach the needle shield to the device without having to directly grasp the needle shield. However, in order to remove the needle shield, the user must directly pinch the clips, which may expose a user to an inadvertent needle stick during recoil. While the device of Deal can be operated solely by hand, the user is provided with little protection when removing the needle shield from the syringe assembly.

WO 03/051423 discloses a hand operated, needle shield removal tool comprising a cylindrical cavity, a top guard plate, and a bottom base plate. The top guard plate is parallel to the bottom base plate, and both plates are perpendicular to, and centered on, the cylindrical cavity. A syringe with a needle shield is inserted into a proximal end of the cylindrical cavity, and the needle shield is gripped by a plurality of spring-like fingers so that when the syringe is pulled upwardly the needle shield is removed. The arrangement of the guard plate and the cylindrical cavity puts the user's hand immediately adjacent to the proximal end of the cylindrical cavity. With the guard plate having such a small surface area, any reflex during detachment potentially causes the uncovered portion of the user's fingers to be inadvertently stuck by the needle.

Accordingly, there is a continuing need for an improved hand operated needle shield removal tool that overcomes, alleviates, or mitigates one or more of the aforementioned drawbacks and deficiencies of the prior art. The present invention addresses the aforementioned problems by providing a pull ring integrally formed to an attachment cavity that engages and holds a needle shield. The pull ring facilitates the removal of a needle shield for users having reduced manual dexterity while also reducing recoil to minimize the potential for needle sticks.

BRIEF SUMMARY OF THE INVENTION

Briefly stated, a preferred embodiment of the present invention comprises a removal tool for a needle shield. The tool includes an attachment cavity having an interior wall extending along a length of the attachment cavity and accessible via a sidewall aperture. The interior wall is sized to receive and engage the needle shield. A pull ring is connected to and extends from a proximal end of the attachment cavity. The pull ring has an exterior wall extending along an outer circumference of the pull ring and an interior wall extending along an inner circumference of the pull ring. The inner circumference is sized to accommodate at least one finger of a user.

Another embodiment of the present invention comprises a needle shield assembly including a needle shield having an outer diameter, a distal end configured to cover a needle, and a proximal end opposite the distal end. A removal tool includes an attachment cavity having an interior wall extending along a length of the attachment cavity and accessible via a sidewall aperture. The interior wall complementarily receives and engages the needle shield. A pull ring is connected to and extends from a proximal end of the attachment cavity. The pull ring has an exterior wall extending along an outer circumference of the pull ring and an interior wall extending along an inner circumference of the pull ring. The inner circumference is sized to accommodate at least one finger of a user.

BRIEF DESCRIPTION OF THE SEVERAL VIEWS OF THE DRAWINGS

The foregoing summary, as well as the following detailed description of a preferred embodiment of the invention, will be better understood when read in conjunction with the appended drawings. For the purpose of illustrating the invention, there are shown in the drawings an embodiment which is presently preferred. It should be understood, however, that the invention is not limited to the precise arrangements and instrumentalities shown.

In the drawings.

DETAILED DESCRIPTION OF THE INVENTION

Figure 1:
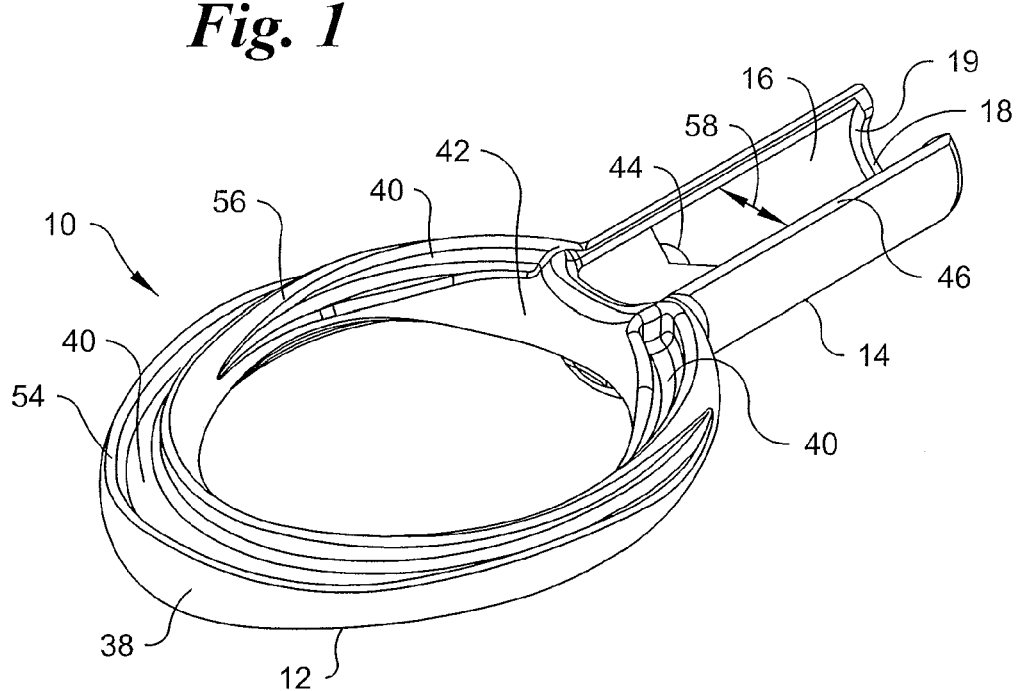
FIG. 1 is a top front perspective view of a needle shield removal tool in accordance with a preferred embodiment of the present invention.

Certain terminology is used in the following description for convenience only and is not limiting. The words "right," "left," "lower" and "upper" designate directions in the drawings to which reference is made. The words "inwardly" and "outwardly" refer to directions toward and away from, respectively, the geometric center of the piston and designated parts thereof. Unless specifically set forth herein, the terms "a", "an" and "the" are not limited to one element but instead should be read as meaning "at least one". The terminology includes the words noted above, derivatives thereof and words of similar import.

Figure 2:
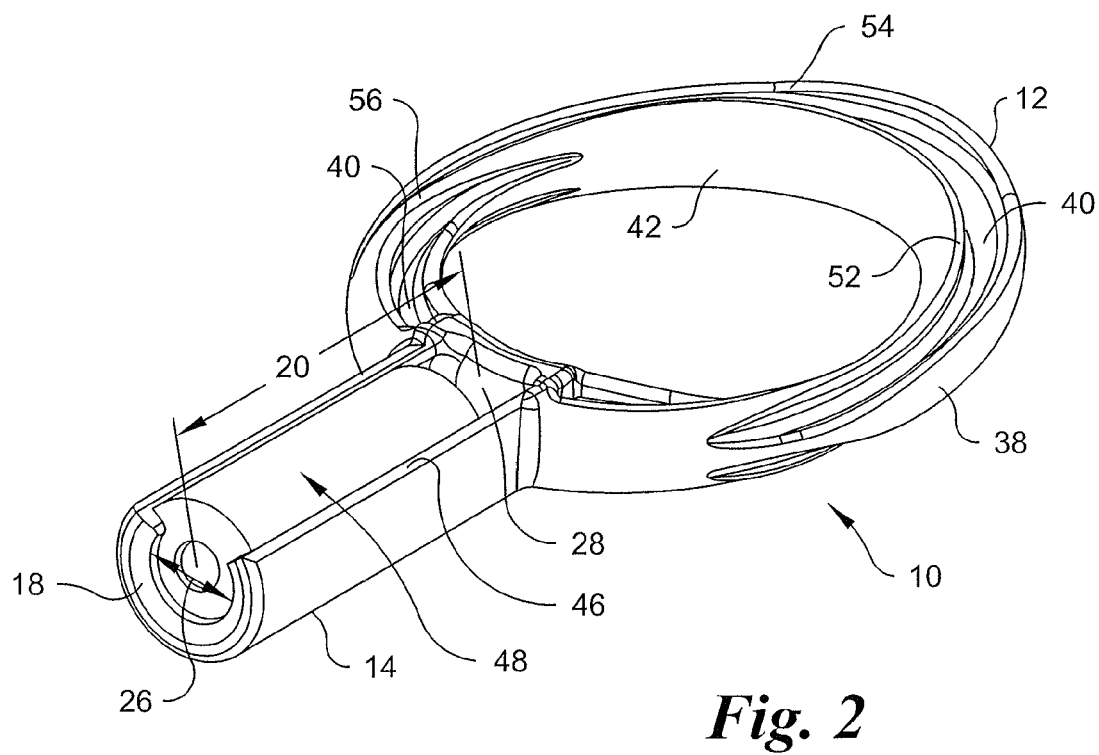
FIG. 2 is a top rear perspective view of the needle shield removal tool of FIG. 1, attached to a needle shield.

Referring to the drawings, there is shown a needle shield removal tool 10 in accordance with a preferred embodiment of the present invention. The needle shield removal tool 10 comprises two principal components, a pull ring 12 and an attachment cavity 14, which may be engaged with a needle shield 48 of a syringe, as shown in FIG. 2. The present invention is usable for removal of a generally cylindrical elongated needle shield 48 from a syringe (not shown). Such needle shields 48 are held onto the distal end of a syringe by an interference or frictional fit. It should be clearly understood that the present invention is not limited to the below described embodiment.

Figure 3:
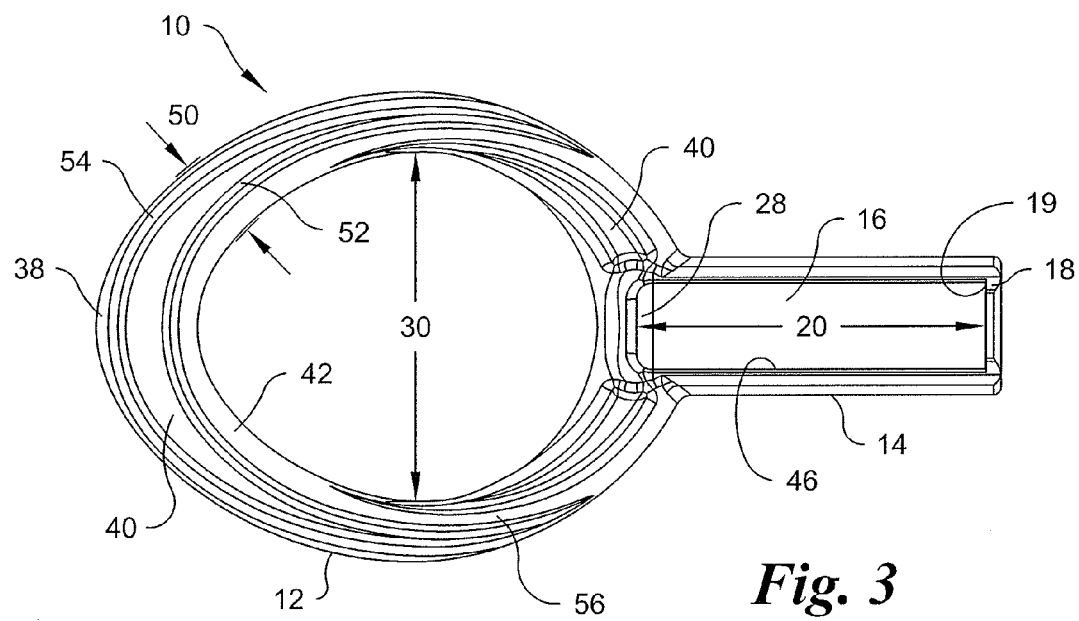
FIG. 3 is a top plan view of the needle shield removal tool of FIG. 1.
Figure 4:
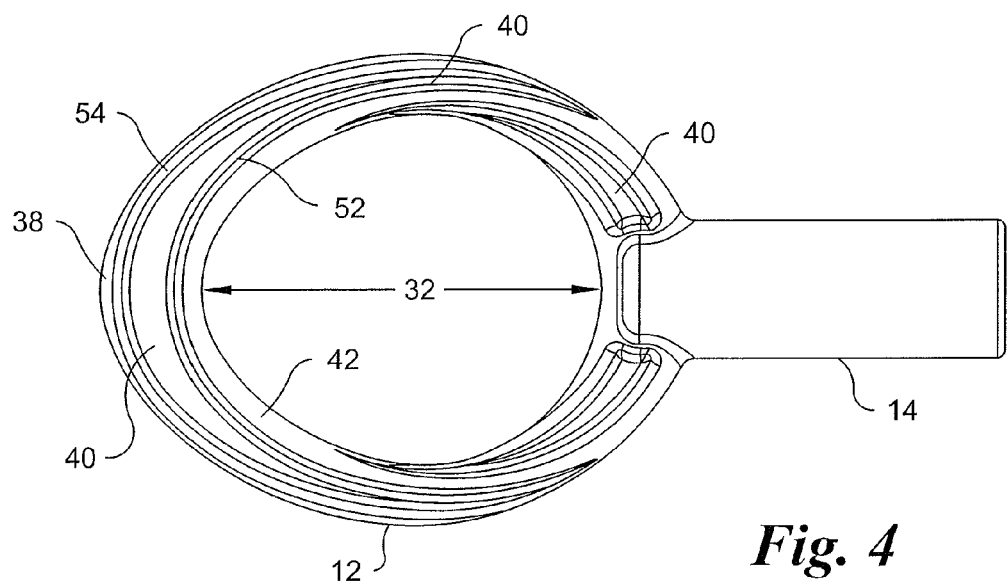
FIG. 4 is a bottom plan view of the needle shield removal tool of FIG. 1.

Referring to FIGS. 3 and 4, the pull ring 12 in the present embodiment is generally oblong or ellipsoidal and has a minor axis length 30 and a major axis length 32. The length of the major axis 32 provides a safeguard distance that separates a user's fingers from a needle tip of a syringe (not shown), which is exposed during removal of the needle shield 48. It will be appreciated by those skilled in the art that the minor axis 30 and major 32 axis can alternate positions, and the lengths of the minor axis 30 and major axis 32 can be equal, creating a circle. The pull ring 12 may also be triangular, square, rectangular, trapezoidal, or some other shape. The pull ring 12 in the present embodiment has a radial thickness 50 and a height or axial thickness 36, both of which may vary along the circumference of the pull ring 12 if desired. It will be appreciated by those skilled in the art that the thickness 50, height 36, major axis length 32, and minor axis length 30 may all vary in size, but preferably are selected such that the user may comfortably and securely extend one or more fingers through the pull ring 12 to grip the pull ring 12 when removing a needle shield 48 from a syringe barrel as described below.

Referring to FIGS. 1 and 2, the pull ring 12 has an interior wall 42 suitable for finger placement during use, which runs along the inner-circumference of the pull ring 12. The interior wall 42 may have a surface that is smooth, dimpled, cross-hatched, or some other topography. The interior wall 42 meets an interior top surface 52 to form a corner, which may be square, rounded, or some other shape. The pull ring 12 further comprises an exterior wall 38, which also meets an exterior top surface 54 to form a corner that may be square, rounded, or some other shape. The exterior wall 38 runs along the outer-circumference of the pull ring 12, and may also have a surface that is smooth, dimpled, cross-hatched, or some other topography.

Figure 5:
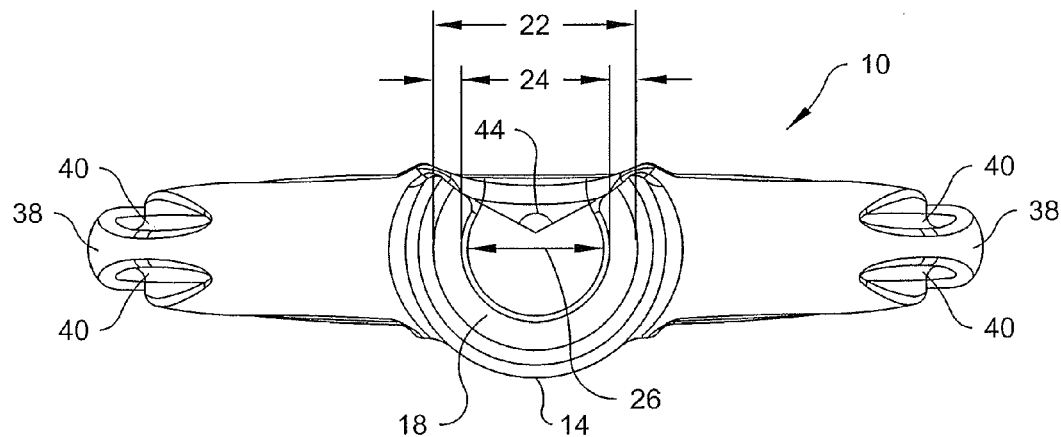
FIG. 5 is an enlarged rear elevational view of the needle shield removal tool of FIG. 1.
Figure 6:
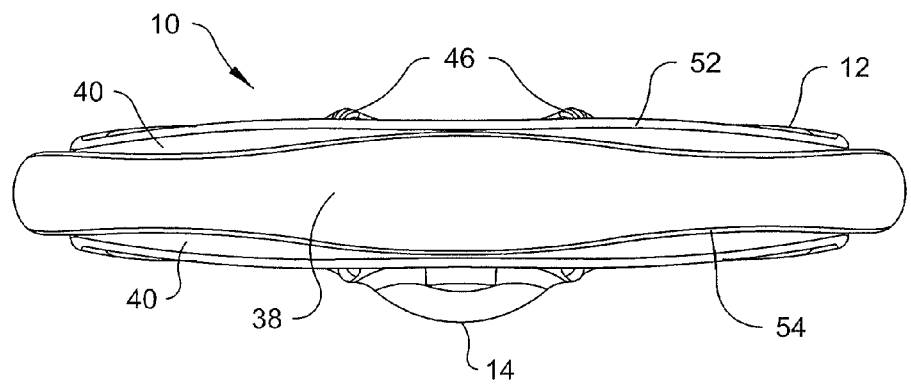
FIG. 6 is an enlarged front elevational view of the needle shield removal tool of FIG. 1.
Figure 7:
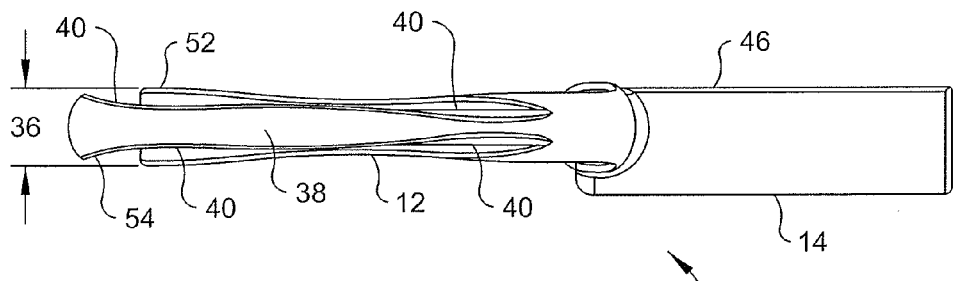
FIG. 7 is an enlarged side elevational view of the needle shield removal tool of FIG. 1.

A generally U-shaped, tapered cavity 40 is positioned between the exterior top surface 54 and the interior top surface 42 of the pull ring 12. A similar cavity 40 may also be provided on the bottom or both the top and bottom surfaces of the pull ring 12, as shown in FIG. 5. The cavities 40 reduce the amount of material required to produce the needle shield removal tool 10 while also creating a valley between the exterior wall 38 and the interior wall 42. The valley provides additional surface area for the user to grip while operating the needle shield removal tool 10 in accordance with the present invention.

An intermediate wall 56 may be positioned between the interior wall 42 and the exterior wall 38. It will be appreciated by those skilled in the art that the placement of the intermediate wall 56 may vary along the circumference of the pull ring 12. Placing one or more intermediate walls 56 in the cavity 40, between the exterior wall 38 and the interior wall 42, may split a single valley into two or more valleys. The intermediate wall 42 may be on the top surface, bottom surface, or both the top and bottom surfaces of the pull ring 12.

Referring to FIGS. 1, 2, and 3, the attachment cavity 14 is suitable for receiving and engaging a needle shield 48. The attachment cavity 14 comprises a sidewall aperture 44, which, in plan view, is a generally rectangular shaped opening, and reveals an interior wall 16 of the attachment cavity 14. The sidewall aperture 44 may also be trapezoidal, ellipsoidal, or some other shape, but preferably is suitably shaped to receive a needle shield 48. The opening created by the sidewall aperture 44 spans the length 20 of the attachment cavity 14 and preferably at most about 50% of the circumference of the attachment cavity 14. Aperture lips 46 span the length 20 of the sidewall aperture 44. The aperture lips 46 may be square, rounded, or some other shape. A distance 58 between the aperture lips 46 is preferably about the same size or at least slightly smaller than the outer diameter of the needle shield 48. The distance 58 between aperture lips is circumferentially large enough to receive the needle shield 48, but the distance 58 is also circumferentially small enough to provide the frictional retention necessary to prevent the installed needle shield 48 from being inadvertently dislodged from the attachment cavity 14 during removal from the syringe barrel.

Referring to FIGS. 1, 2, 3, and 5, the length 20 of the attachment cavity 14 extends from a base wall 28, which is proximate to the pull ring 12, to a collar stop 18. The length 20 of the attachment cavity 14 is at least slightly greater than the length of the needle shield 48, but may vary in some applications. The base wall 28 and the collar stop 18 are both generally perpendicular to the inner cavity wall 16, as shown in FIGS. 2 and 3. A collar aperture 26 located at the center of the collar stop 18, and may be circular, square, rectangular, ellipsoidal, or some other shape, but preferably is shaped to receive a portion of a syringe barrel. The collar stop 18 has a width 24 that spans from the inner cavity wall 16 to the collar aperture 26, as shown in FIG. 5.

Referring to FIGS. 1, 2, 3, and 5 an inner diameter 22 of the attachment cavity 14, which is measured at the inner cavity wall 16, is preferably the same or at least slightly greater than the outer diameter of the needle shield 48. The collar aperture 26 is at least slightly smaller than the outer diameter of a needle shield 48 so that a proximal end 34 of an installed needle shield 48 engages a distal end 19 of the collar stop 18, as shown in FIGS. 1 and 2. The width 24 of the collar stop 18 is preferably small enough to provide a clearance between a distal end of the syringe barrel and the collar aperture 26.

In use, the needle shield 48 is first centered on the aperture lips 46 of the attachment cavity 14 with the distal end of the needle shield 48 at or near the base wall 28 and the proximal end of the needle shield 48 at or near the distal end 19 of the collar stop 18. Because the distance 58 between the aperture lips 46 is the same or slightly less than the exterior diameter of the needle shield 48, the user must press the needle shield 48 so that the aperture lips 46 spread apart at least slightly. With sufficient pressure from the user's fingers, the needle shield 48 is installed into the attachment cavity 14 by passing through the aperture lips 46 and snapping into the attachment cavity 14. When positioning the needle shield 48 against the aperture lips 46, the proximal end of the needle shield 48 must be at or adjacent to the distal side 19 of the collar stop 18 with the syringe barrel in the collar aperture 26 (not shown). The attachment cavity 14 secures the needle shield 48 by engaging the distal end 19 of the collar stop 18 with the proximal end of the needle shield 48. Once inserted, the user places one or more fingers of one hand inside of the pull ring 12 while holding the syringe barrel with the other hand and leverages the interior wall 42, pulling the needle shield removal tool 10 in accordance with the present invention away from the syringe and separating the needle shield 48 from the syringe barrel.

The cavities 40 provide additional surface area on the pull ring 14, enhancing the user's grip. Better control over the pull ring 12 combined with the safeguard distance provided by the major axis 32 of the pull ring 12, which separates the user's fingers from the exposed needle tip, prevents inadvertent needle sticks of the hand holding the pull ring 12 during removal of the needle shield 48.

The needle shield removal tool 10 in accordance with this invention can be manufactured by injection molding polymeric materials include polyethylene, polypropylene, polyurethane, polysiloxane, or other suitable materials. The proximal end of the pull ring 12 is preferably integrally formed with the exterior distal end of attachment cavity 14. The arrangement of pull ring 12 and attachment cavity 14 allows polymeric materials to be injection molded as a single shot. Therefore all of the needle shield removal tool components are integrally formed as a single piece, providing cost-effective and robust manufacturing processes. If desired, the attachment cavity 14 and the pull ring 12 may be separately formed and thereafter secured together in any suitable manner.

From the foregoing, it can be seen that the present invention comprises a tool for attaching to syringes to facilitate the removal of a needle shield. It will be appreciated by those skilled in the art that changes could be made to the embodiment described above without departing from the broad inventive concept thereof. It is understood, therefore, that this invention is not limited to the particular embodiment disclosed, but it is intended to cover modifications within the spirit and scope of the present invention as defined by the appended claims.

What is claimed is:

1. A removal tool for a needle shield, the tool comprising:
an attachment cavity having an interior wall extending along a length of the attachment cavity and accessible via a sidewall aperture spanning the length of the attachment cavity, between a pair of parallel aperture lips, for receiving the needle shield therethrough, the interior wall being sized to receive and engage the needle shield; and
a pull ring connected to and extending from a proximal end of the attachment cavity, the pull ring having an exterior wall extending along an outer circumference of the pull ring and an interior wall extending along an inner circumference of the pull ring, the inner circumference being sized to accommodate at least one finger of a user, the pull ring further having a U-shaped cavity located between the exterior and interior walls thereof, an opening formed by the U-shaped cavity facing a direction generally perpendicular to a longitudinal extent of the attachment cavity.

2. The removal tool of claim 1, wherein the pull ring has an ellipsoidal shape defined by major and minor axes.

3. The removal tool of claim 2, wherein a size of the major axis is different than a size of the minor axis.

4. The removal tool of claim 1, wherein the pull ring further includes an intermediate wall positioned in the U-shaped cavity.

5. The removal tool of claim 1, wherein a distance between the aperture lips is one of smaller than and equal to an outer diameter of the needle shield.

6. The removal tool of claim 1, wherein the attachment cavity further includes a collar stop connected to a distal end of the attachment cavity, the collar stop being oriented generally perpendicularly to the interior wall of the attachment cavity.

7. The removal tool of claim 6, further comprising a collar aperture located at a center of the collar stop.

8. The removal tool of claim 1, further comprising a base wall located at the proximal end of the attachment cavity and oriented generally perpendicularly to the interior wall of the attachment cavity.

9. A needle shield assembly comprising:
 a needle shield having an outer diameter, a distal end configured to cover a needle, and a proximal end opposite the distal end; and
 a removal tool comprising:
  an attachment cavity having an interior wall extending along a length of the attachment cavity and accessible via a sidewall aperture spanning the length of the attachment cavity, between a pair of parallel aperture lips, for receiving the needle shield therethrough, the interior wall complementarily receiving and engaging the needle shield; and
  a pull ring connected to and extending from a proximal end of the attachment cavity, the pull ring having an exterior wall extending along an outer circumference of the pull ring and an interior wall extending along an inner circumference of the pull ring, the inner circumference being sized to accommodate at least one finger of a user, the pull ring further including a U-shaped cavity located between the exterior and interior walls thereof, an opening formed by the U-shaped cavity facing a direction generally perpendicular to a longitudinal extent of the attachment cavity.

10. The assembly of claim 9, wherein the attachment cavity further includes a collar stop at a distal end thereof, the collar stop extending perpendicularly to the interior wall of the attachment cavity and engaging the proximal end of the needle shield when the needle shield is positioned within the attachment cavity of the removal tool.

11. The assembly of claim 10, further comprising a collar aperture located at a center of the collar stop.

12. The assembly of claim 9, wherein the pull ring has an ellipsoidal shape defined by major and minor axes.

13. The assembly of claim 12, wherein a size of the major axis is different than a size of the minor axis.

14. The assembly of claim 9, wherein the pull ring further includes an intermediate wall positioned in the U-shaped cavity.

15. The assembly of claim 9, wherein a distance between the aperture lips is one of smaller than and equal to the outer diameter of the needle shield.

16. The assembly of claim 9, wherein the removal tool further comprises a base wall located at the proximal end of the attachment cavity and oriented generally perpendicularly to the interior wall of the attachment cavity.

* * * * *